United States Patent [19]
Yen et al.

[11] Patent Number: 5,456,724
[45] Date of Patent: Oct. 10, 1995

[54] LOAD SENSOR FOR BONE GRAFT

[75] Inventors: Hung-Ju Yen; Chih-Ming Wu; Wei-Tai Jao; Chen-Dao Shiao, all of Chutung; Chi-Ming Shih, Hsinchu; Cheng-Kung Cheng, Chutung; Tze-Hong Wong; Kou-Shung Sheh, both of Hsinchu, all of Taiwan

[73] Assignee: Industrial Technology Research Institute, Hsinchu, Taiwan

[21] Appl. No.: 167,700

[22] Filed: Dec. 15, 1993

[51] Int. Cl.$^6$ .............................. A61F 2/28; A61F 2/44; A61F 2/46

[52] U.S. Cl. .............................. 623/16; 623/17; 128/781; 73/862.635; 606/102

[58] Field of Search .............................. 623/16–17, 20, 623/18, 24; 73/862.635, 862.633, 862.632, 855, 172; 128/781; 606/102

[56] References Cited

U.S. PATENT DOCUMENTS

| | | | |
|---|---|---|---|
| 2,440,706 | 5/1948 | Tint | 73/862.635 X |
| 3,240,065 | 3/1966 | Taber | 73/862.635 X |
| 3,315,203 | 4/1967 | Jacobson | 73/862.635 X |
| 3,535,923 | 10/1970 | Martorana et al. | |
| 3,938,379 | 2/1976 | Bingham | 73/863.633 |
| 4,065,962 | 1/1978 | Shoberg | 73/862.635 X |
| 4,282,762 | 8/1981 | Zenker | 73/862.635 X |
| 4,576,158 | 3/1986 | Boland | 606/102 |
| 4,899,761 | 2/1990 | Brown et al. | |
| 5,056,374 | 10/1991 | McMennamy et al. | 73/862.635 X |
| 5,125,408 | 6/1992 | Basser | 128/774 X |
| 5,197,488 | 3/1993 | Kovacevic | 128/782 |

FOREIGN PATENT DOCUMENTS

| | | | |
|---|---|---|---|
| 0252762 | 12/1987 | German Dem. Rep. | 623/25 |
| 0451929 | 11/1974 | U.S.S.R. | 73/862.635 |
| 0856449 | 8/1981 | U.S.S.R. | 606/102 |
| 0963504 | 10/1982 | U.S.S.R. | 606/102 |

OTHER PUBLICATIONS

Sanders et al., "Measurement of Stresses in Three Orthogonal Directions at the Residual Limb–Prothetic socket Interface", IEEE Transactions on Rehabilitation Engineering, vol. 1, No. 2, Jun. 1993, pp. 79–85.

*Primary Examiner*—David H. Willse
*Attorney, Agent, or Firm*—Christie, Parker & Hale

[57] ABSTRACT

A load sensor inserted between two bones for sensing a stress exerted on the load sensor includes a body, and a load transducer mounted in the body for transducing a strain thereof resulting from the stress into an electronic signal. Such load sensor can detect a stress exerted on a bone graft bone and/or the interaction of the bone graft and spine implant to improve curative effects and increase the successful rate of a bone graft operation.

26 Claims, 9 Drawing Sheets

LOAD SENSOR FOR BONE GRAFT

BACKGROUND OF THE INVENTION

The present invention relates generally to a load sensor, and more particularly to a load sensor for a bone graft. Because of the pathological changes or the explosive fractures, a certain part of the abnormal bone has to be excised. Taking the spine for example, after the abnormal part of the spine has been excised or excavated, the spine implant and the interbody bone graft have to be applied. Currently, the bone graft is performed only by the doctor's clinical experience, and there is no related objective data for the doctor's reference in performing the bone graft. To improve the bone graft technique, it is necessary to provide a reliable load sensor device for the clinician in order that the real stressed status of the bone graft and the interaction between the bone graft and the spine implant can be easily detected.

It would be desirable if:

a) During operation, there is a load sensor which can be applied to help the doctor to understand the real stressed status of the bone graft, so that the bone graft can be implanted more effectively.

b) In the simulating experiment of implanting the bone graft, there is a load sensor which can be placed in the bone and can be operated for substituting the bone graft and can include therein a stress-sensing device for sensing the stress distribution of different kinds of the spine implants and the bone grafts under various pre-stressed conditions to which the clinician can refer.

It is therefore attempted by the Applicant to devise such load sensor as above described.

SUMMARY OF THE INVENTION

The primary object of the present invention is to provide a load sensor which can detect a stress exerted on a bone graft.

A further object of the present invention is to provide a load sensor to inspect the interaction between a bone graft and a spine implant.

A yet object of the present invention is to provide a load sensor to provide the clinician with reference data for grafting a bone graft.

Still an object of the present invention is to provide a load sensor capable of simulating the size of a bone graft.

One more object of the present invention is to provide a load sensor capable of rendering stimulating effects of a bone graft.

Still more object of the present invention is to provide a load sensor capable of prestressing a bone graft.

Yet more object of the present invention is to provide a load sensor capable of measuring the magnitude of the force exerted on a bone graft after the bone graft has been grafted.

Further more object of the present invention is to provide a load sensor capable of improving curative effects for an operation of grafting a graft bone.

The other object of the present invention is to provide a load sensor capable of improving the reliability of an operation of grafting a bone graft.

In accordance with the present invention, a load sensor to be inserted between two bones for sensing a stress exerted on the load sensor includes a body, and a load transducer mounted in the body for transducing a strain thereof resulting from the stress into an electronic signal to be transmitted to an analyzer for analyzing the stress exerted on the load sensor.

Certainly, the analyzer can include a computer or an indicator. The body can include a first post with a relatively smaller diameter and with a male screw thread, and a second post with a relatively larger diameter and generally connected coaxially to the first post. The second post can further contain therein the load transducer.

Certainly, the load sensor can further include a length-adjusting device mounted on one end of the body for adjusting a length of the load sensor. The length-adjusting device can include a hollow tube provided with a female screw thread engageable with the male screw thread for adjusting the length of the load sensor, a first positioning device mounted on one end of the hollow tube for permitting the one end of the load sensor to be fixed with one of the two bones and for automatically producing an aligning effect. Certainly, the second post and the hollow tube can be respectively provided with knurled surfaces for conveniently adjusting the length of the load sensor.

Certainly, the length-adjusting device can be fixed by a blocking device when the length is adjusted to a desired extent. The blocking device can include at least one bolt.

Certainly, the first post can be processed to have a longitudinal plane surface in order that the male screw thread will not be damaged when the at least one bolt is to fix the length-adjusting device firmly, and an undesired material can be discharged along the plane surface.

Certainly, the load sensor can further comprise a fixing device including a first disk held attached closely to the load transducer for protecting and shielding the load transducer from an undesired communication interference, a second disk having a relatively larger diameter and connected to the first disk for protecting the load transducer and a bottom of the body and for enlarging a force-receiving area, and a second positioning device connected to the second disk for permitting the load sensor to be fixed with another one of the two bones and for automatically providing an aligning effect.

Certainly, the first and second positioning devices can respectively be protrusions with an arc end, with a pointed end, or with a claw-shaped end.

Certainly, the load transducer can include a transducer body for resulting in the strain produced thereon when subject to the stress, and plural strain gages mounted on the transducer body for sensing the strain. The transducer can have a pair of planes on two opposite sides thereof and an egg-shaped hole therein. The egg-shaped hole and the pair of planes can form thereby two thinnest portions of the transducer body. The two thinnest portions can respectively have two outer surfaces and two inner surfaces. The number of the plural strain gages can be four. The four strain gages can respectively be located on the positions. The load transducer can be piezoelectric or inductive.

Certainly, the two bones can be two parts of a fractured bone or two segments of a patient's spine. The two bones can be two parts of an ill bone. The two bones can be partially separated.

The present invention can be more fully understood by reference to the following description and accompanying drawings which form an integral part of this application.

DETAILED DESCRIPTION OF THE PREFERRED EMBODIMENTS

Figure 1:
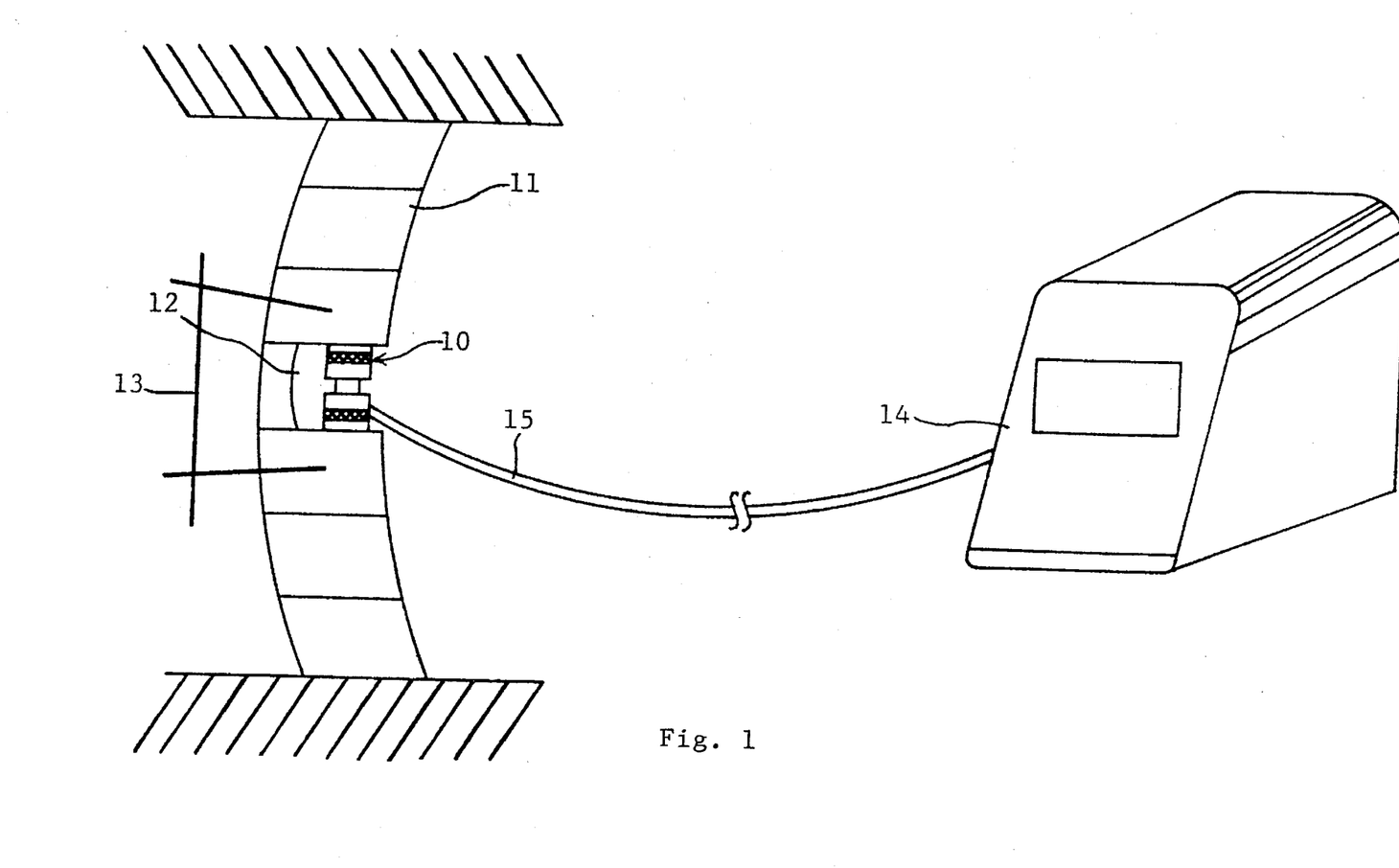
FIG. 1 shows the application of a load sensor according to the present invention.

One application of a preferred embodiment of a load sensor according to the present invention is shown in FIG. 1. The size and the shape of the present load sensor are generally the same as those of a bone graft, and the load sensor is implanted in the excised part of a spine or two segments of a fractured bone to substitute the bone graft temporarily. FIG. 1 shows that the present load sensor 10 is installed in the excised part 12 of a spine specimen 11 and the spine implant 13 is also in place. The spine specimen 11 is mounted on a material testing machine to simulate possible actions of the spine and for detecting the stress exerted on the bone graft. The stress is then converted into an electronic signal, and the electrical signal is transmitted to an analyzer 14 including a computer or an indicators through a signal wire 15 for analyzing the signal.

Figure 2:
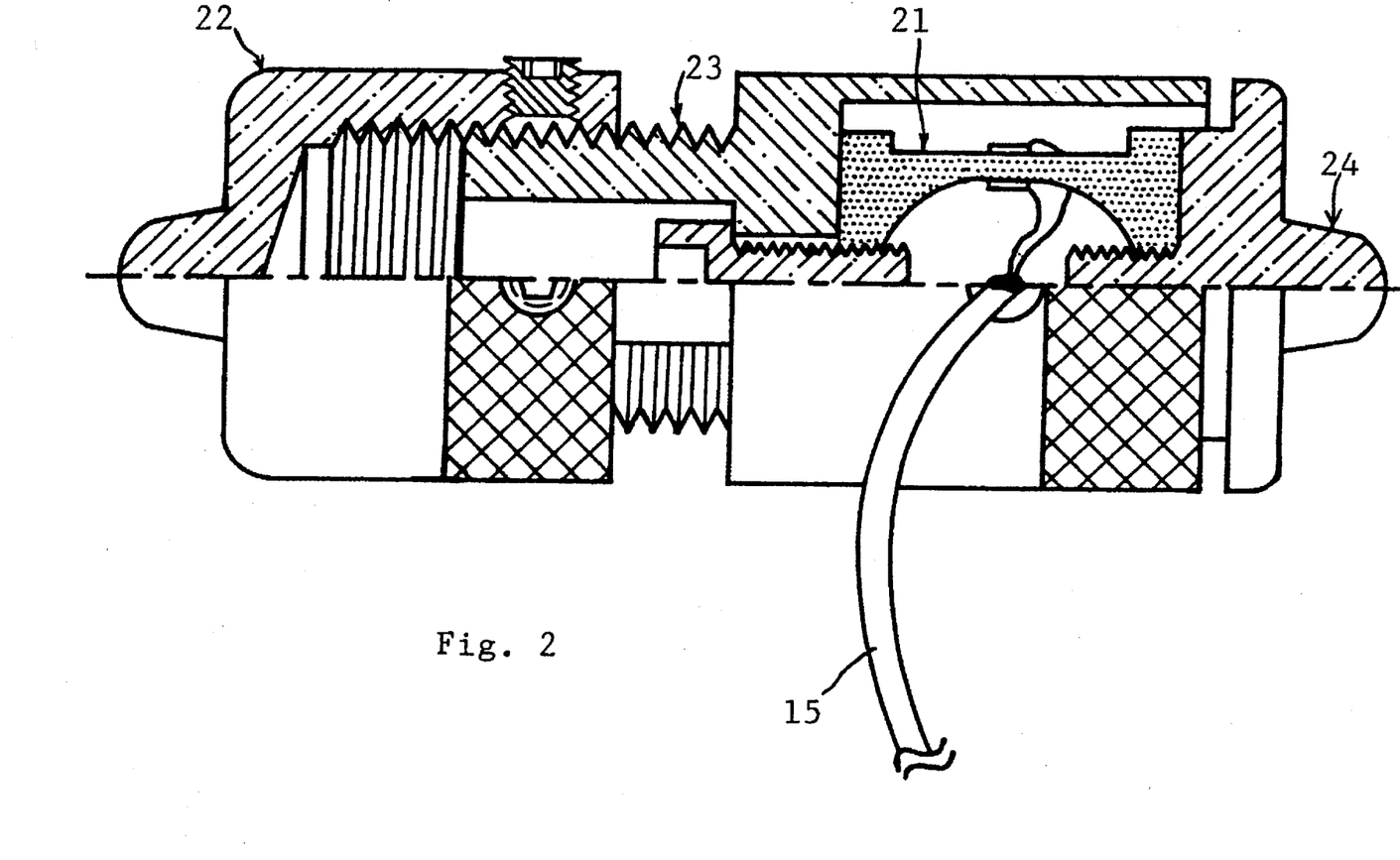
FIG. 2 is a sectional view of a load sensor according to the present invention.

To match the actual size of the excised part, the present load sensor whose outer diameter is 17 mm and which can be adjusted to have a desired length ranging from 37 mm to 44 mm is depicted in FIG. 2. The present load sensor chiefly includes a load transducer 21, a length-adjusting device 22, a body 23 and a fixing device 24.

Figure 3A:
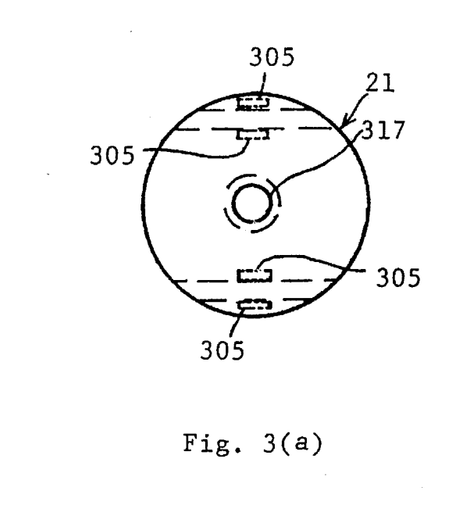
FIGS. 3(a) & 3(b) are respectively sectional and top views of a load transducer of a load sensor according to the present invention.
Figure 3B:
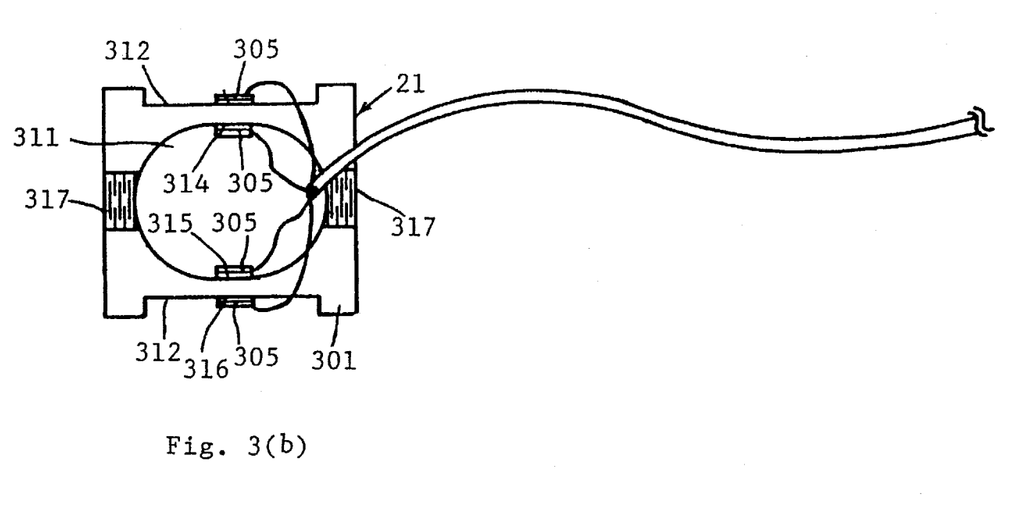

The load transducer 21 in FIG. 2–FIG. 3(b) is a strain gage-based load transducer. The detailed arrangement of strain gage-based load transducer 21 is shown in FIG. 3. The transducer body 301 is a cylinder with a diameter 12 mm and a height 13 mm. The transducer body 301 is processed to have an egg-shaped hole 311 and a pair of symmetrical planes 312. Then, the egg-shaped hole 311 and the pair of symmetrical planes 312 will form thereby two thinnest portions of the transducer body 301. The two pairs of the outer and inner surfaces 313, 314, 315, 316 of the thinnest portions are respectively installed thereon with four strain gages 305. Besides, there are two screw holes 317 provided in the transducer body 301 for connecting the body 23 with the fixing device 24.

By the special design of the transducer body 301 as mentioned above, the strain gages 305 attached to the surfaces 313, 314, 315, 316 can sense the stress most sensitively.

The strain gage 305 is a resistor element whose resistance will be linearly varied according to the deformation of the surface where the strain gage is attached. For example, when the surface where the strain gage 305 is attached is tensilely deformed, the resistance of the strain gage 305 will be increased, and when the surface where the strain gage 305 is attached is compressively deformed, the resistance of the strain gage 305 will be decreased. That is to say, when the resistance of the strain gage 305 is originally R, the resistance becomes $R+\Delta R$ when the strain gage 305 senses the tensile deformation, and the resistance becomes $R-\Delta R$ when the strain gage 305 senses the compressive deformation.

The transformation formula expressing the relationship between the deformation and the strain is shown as follows:

$$\epsilon = \Delta L/L \qquad (a),$$

wherein $\epsilon$: the strain of an object's surface;

L: the original length of the object's surface;

$\Delta L$: the variation in the length of the object's surface when the object is exerted by a force.

Therefore, the relation between the resistance of the strain gage 305 and the strain of the object's surface where the strain gage 305 is attached is shown as follows:

$$(\Delta R/R) = F \times \epsilon \qquad (b),$$

wherein

F: the strain factor;

R: the original resistance of the strain gage 305;

$\Delta R$: the resistance variation resulting from the deformation sensed by the strain gage 305.

Figure 4:
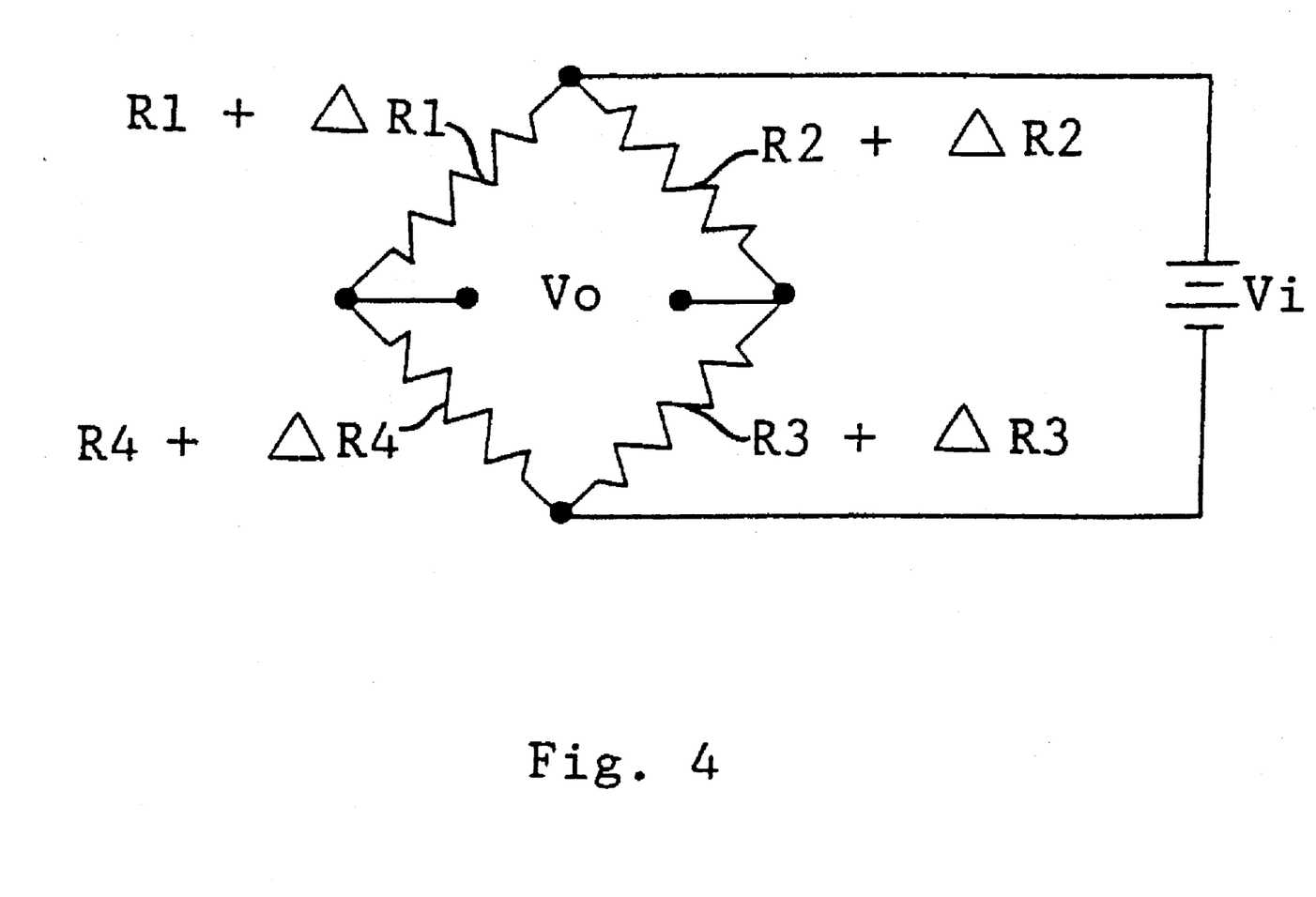
FIG. 4 shows a Wheatstone bridge circuit for a load sensor according to the present invention.

If four strain gages 305 having resistance R1, R2, R3, R4 of the same original value are attached to the transducer body 301 and are connected to form a Wheatstone bridge circuit as shown in FIG. 4, the resistances of the four strain gages 305 will become $R1+\Delta R1$, $R2+\Delta R2$, $R3+\Delta R3$, $R4+\Delta R4$, after an excitation voltage Vi power-supplies the circuit and after the load transducer subject to a force deforms. According to the theory of the Wheatstone bridge circuit, the variation of the resistance can be transformed into the variation of the potential (i.e., the output signal), and the relation is:

$$Vo = \left( \frac{Vi}{4} \right) \times \left( \frac{\Delta R1}{R1} - \frac{\Delta R2}{R2} + \frac{\Delta R3}{R3} - \frac{\Delta R4}{R4} \right), \text{ wherein} \qquad (c)$$

Vo: the output signal (voltage) of the bridge circuit;

Vi: the excitation voltage of the bridge circuit;

R1, R2, R3, R4: the resistances of the four strain gages 305;

$\Delta R1$, $\Delta R2$, $\Delta R3$, $\Delta R4$: the resistance variations of the strain gages 305 after the transducer body 301 is deformed.

If the transducer body 301 is processed as above and the four strain gages 305 are installed as above, the pair of $\Delta R1$ and $\Delta R3$ and the pair of $\Delta R2$ and $\Delta R4$ will be with opposite signs (i.e., one pair is negative, and the other pair is positive). Therefore, the largest output signal of the Wheatstone bridge circuit can be obtained since what are bracketed in equation (c) will be additively summed.

Taking equation (b) into equation (c), we can further obtain a relation between the output signal and the strain:

$$Vo = \left( \frac{Vi \times F}{4} \right) \times (\epsilon 1 - \epsilon 2 + \epsilon 3 - \epsilon 4), \text{ wherein} \qquad (d)$$

$\epsilon 1$, $\epsilon 2$, $\epsilon 3$, and $\epsilon 4$: the strains of the surfaces where the strain gages 305 are respectively attached.

The relation between the strain and the stress is:

$$\sigma = E \times \epsilon \quad (e),$$

wherein

σ: the stress;

E: the elastic modulus.

Taking equation (e) into equation (d), we can obtain a relation equation between the output signal and the load (i.e., the stress) suffered by the load transducer 21:

$$Vo = \left( \frac{Vi \times F}{4 \times E} \right) \times (\sigma 1 - \sigma 2 + \sigma 3 - \sigma 4), \text{ wherein} \quad (f)$$

σ1, σ2, σ3, and σ4: the stresses exerted on the positions where the strain gages are attached.

Thus, as mentioned above, the load can be transmitted into an electrical signal by the load transducer 21, and after corrected, the signal is transmitted into the indicator 14 for being properly analyzed.

When both ends of the transducer body 301 are subject to the load, the thinnest portions formed by the pair of planes 312 and the egg-shaped hole 311 will obtain the largest strain. Since the variation of the strain in these portions is the largest, it is better that the strain gages 305 are mounted on the thinnest portions for sensing the strain more precisely.

According to FIGS. 3(a) & 3(b), the positions 313, 314, 315, 316 where the strain gages 305 are mounted are depicted therein. When the load is exerted on the load transducer 21, there will be the tensile deformation generated on positions 313 and 316 and corresponding compressive deformation generated on positions 314 and 315. According to what is mentioned above, we can thus precisely obtain the value of the strain.

Figure 5A:
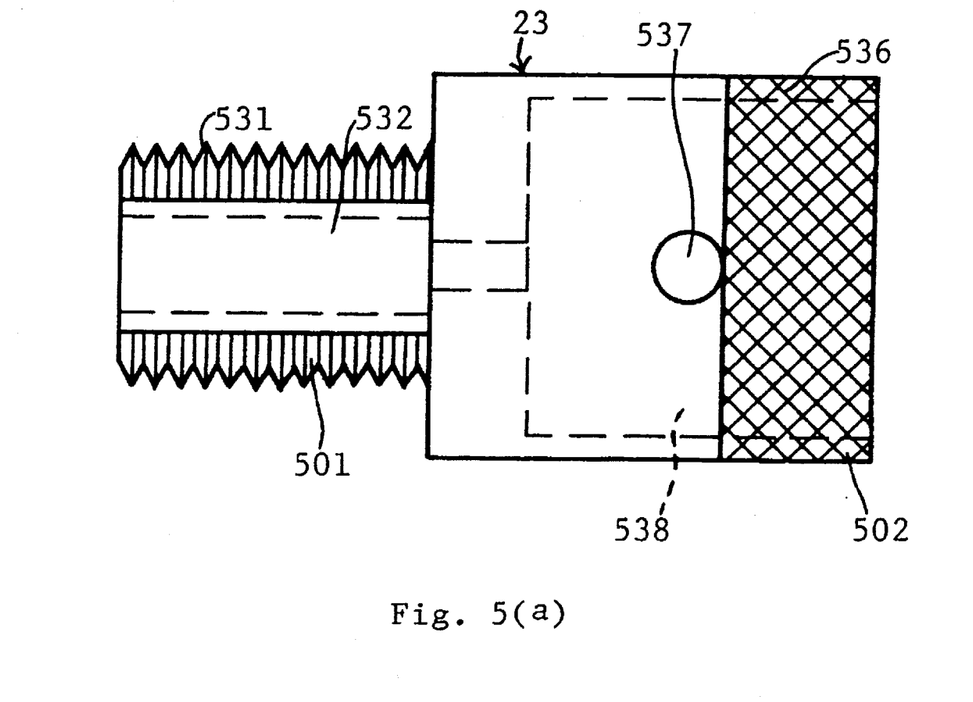
FIGS. 5(a) & 5(b) are respectively elevational and top views of a body of a load sensor according to the present invention.
Figure 5B:
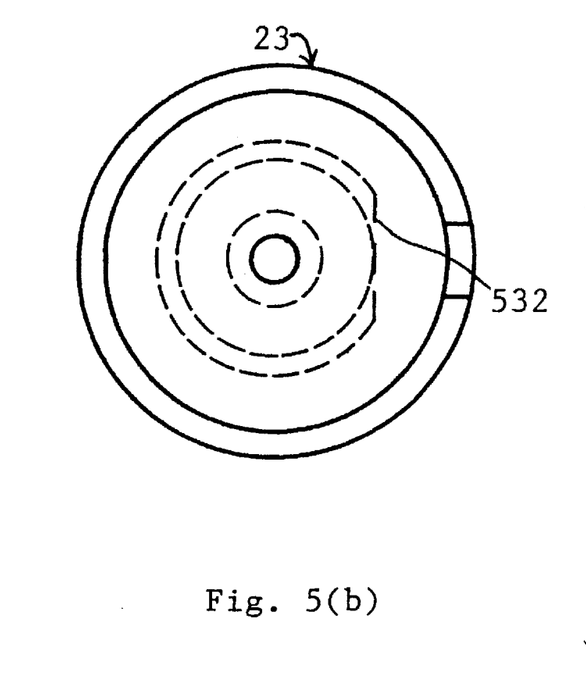

Referring to FIGS. 5(a) & 5(b), the body 23 being a shouldered hollow cylinder includes a first post 501 with a relatively smaller diameter and with a male screw thread 531, and a second post 502 with a relatively larger diameter and generally connected coaxially to the first post 501. There is also a hollow portion 538 formed in the second post 502 and containing therein the load transducer 21. Further, there is a small hole 537 located on the second post 502 for permitting the signal wire 15, connected to the load transducer 21 and the indicator 14, to pass therethrough.

Figure 6A:
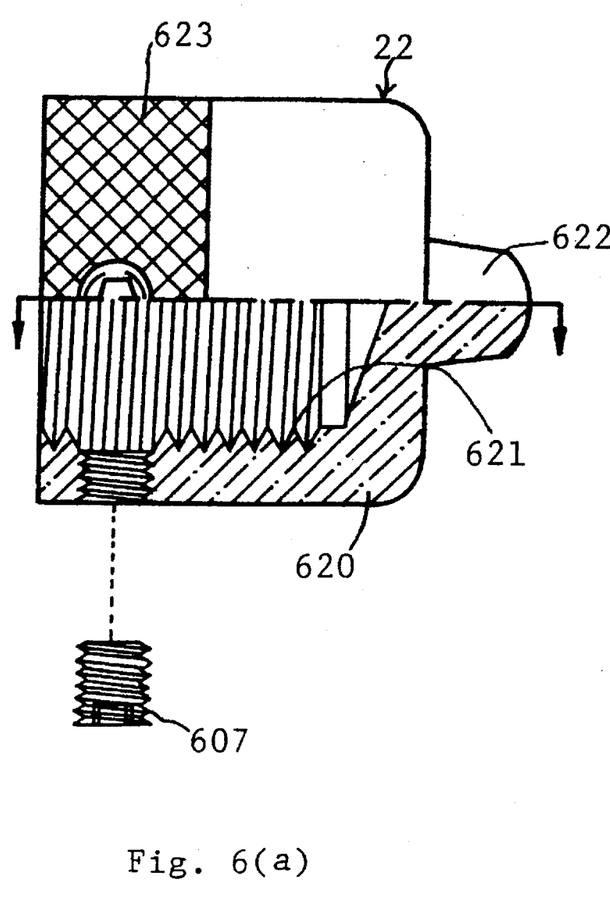
FIGS. 6(a) & 6(b) are respectively sectional and top views of a length-adjusting device of a load sensor according to the present invention.
Figure 6B:
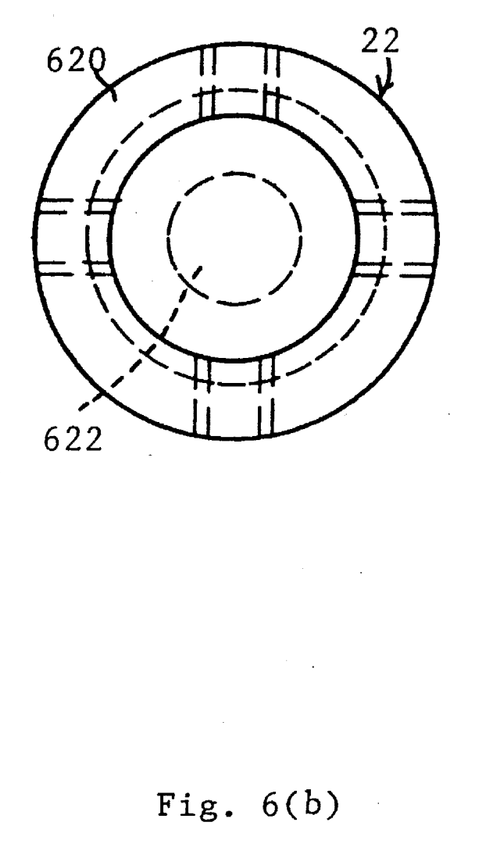

The length-adjusting device 22 is shown in FIGS. 6(a) & 6(b). There is a hollow tube 620 provided with therein a female screw thread 621 engageable with the male screw thread 531 and connected with the body 23 for adjusting the length of said load sensor. The first positioning device 622 is mounted on one end of the hollow tube 620 for permitting one end of the load sensor to be easily fixed in the space resulting from the excised part and for automatically producing an aligning effect. Besides, the outer surface of the hollow tube 620 is processed to have a knurled surface 623 for increasing the friction between the user's fingers and the length-adjusting device 22 and then for more conveniently applying the length-adjusting device 22. Furthermore, there is a blocking device 607 being four bolts distributed every ninety degrees around the circumference of the length-adjusting device 22 and for fixing the length-adjusting device 22 when a desired length is decided.

Referring to FIGS. 5(a)–6(b), it is noted that the first post 501 is processed to have a longitudinal plane surface 532 in order that the male screw thread 531 will not be damaged when the bolts 607 are urged against the first post 501 firmly, and an undesired material such as the blood, fat or flesh can be discharged out along the plane surface 532.

Referring to FIG. 5(a) again, the outer surface of the second post 502 is also processed to have a knurled surface 536 for increasing the friction between the user's fingers and the second post 502 for conveniently applying the length-adjusting device 22.

Figure 7A:
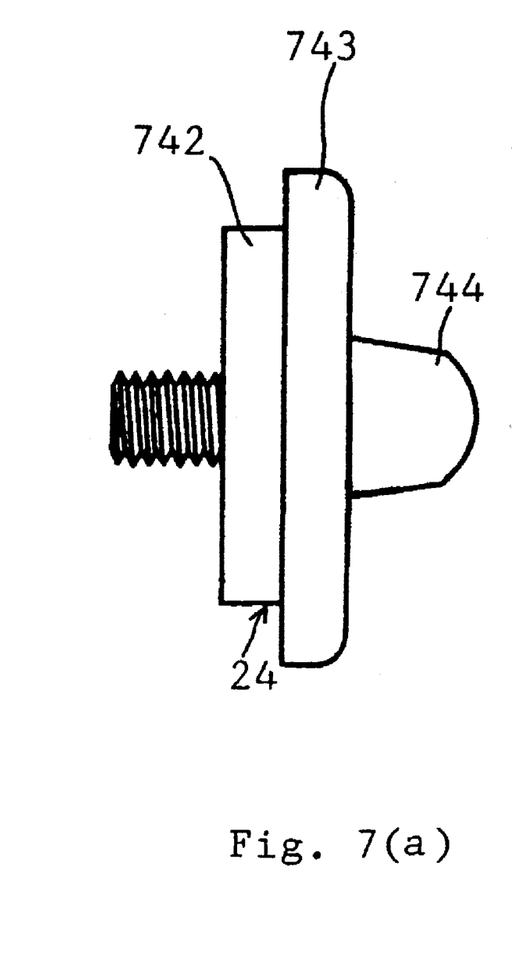
FIGS. 7(a) & 7(b) are respectively elevational and top views of a fixing device of a load sensor according to the present invention.
Figure 7B:
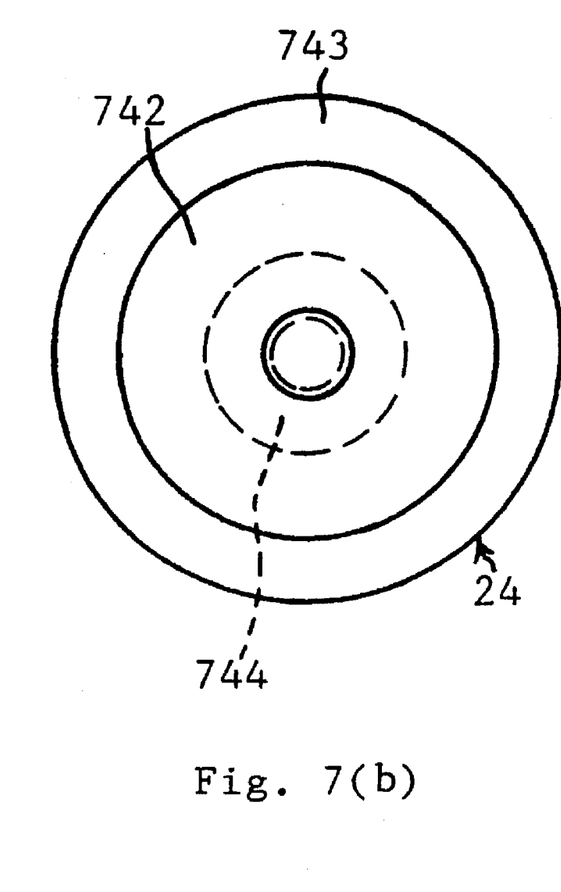
Figure 8A:
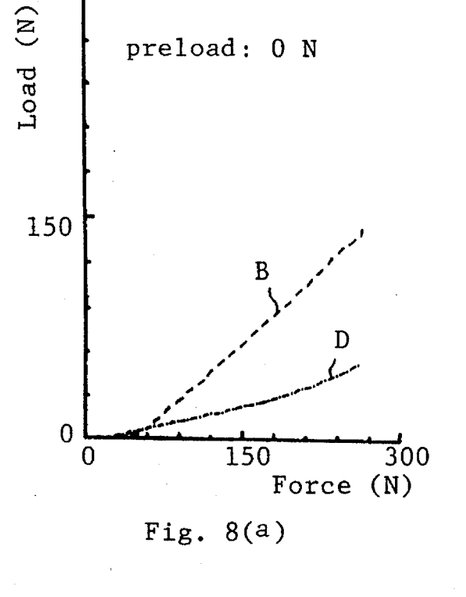
FIGS. 8(a)–8(d) show measured data of the actual stressed status of a bone graft.
Figure 8B:
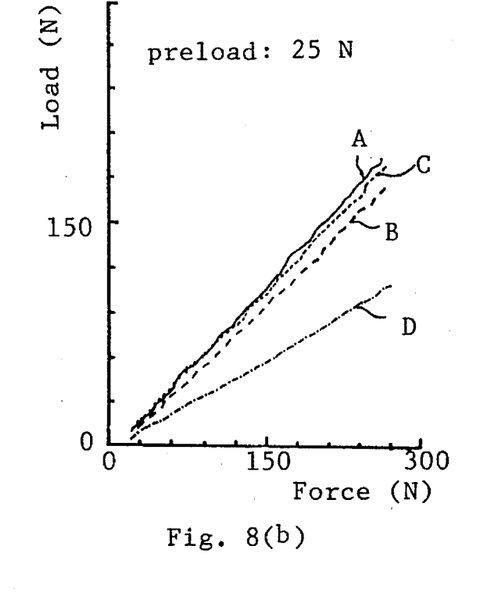
Figure 8C:
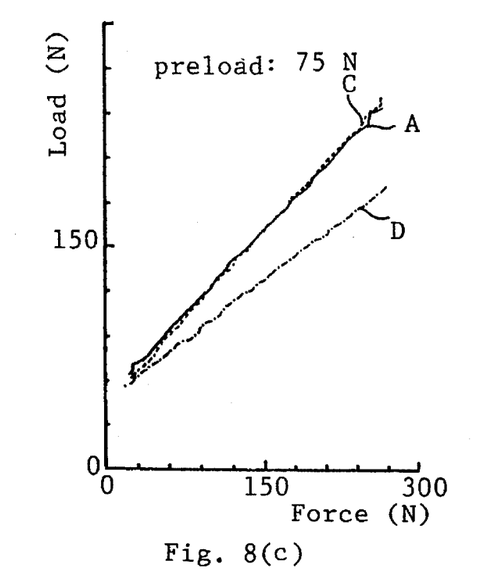
Figure 8D:
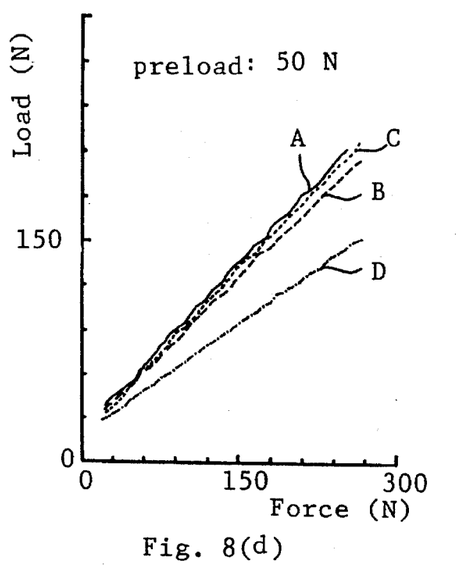

The fixing device 24, as shown in FIGS. 7(a) & 7(b), includes a first disk 742 held attached closely to the load transducer 21 and partly inside the hollow portion 538 for protecting and shielding the load transducer 21 from an undesired communication interference, a second disk 743 having a relatively larger diameter and connected to the first disk 742 for protecting the load transducer 21 and the bottom of the body 23 and for enlarging a force-receiving area, and a second positioning device 744 connected to the second disk 743 for permitting the load sensor 21 to be fixed in the space resulting from the excised part and for automatically providing an aligning effect.

It is to be noticed that the first and second positioning devices 622,744 can be respectively protrusions with an arc end, with a pointed end, or with a claw-shaped end. Referring again to FIG. 1, after the bone fractures because of pathological changes or an explosive fracture is excised and the spine implant are applied, the space resulting from the excised part is reduced because of the squeeze of the spine implant. Therefore, the load sensor can be implanted into the space to substitute the excised part and to prop up the bone part concerned to its original form by the length-adjusting device 22.

There are two exemplarily practical applications of the present load sensor:

a) The load sensor is placed in the excised part of the spine specimen (referring to FIGS. 1 & 2), and the length-adjusting device 22 is adjusted to stretch the excised part, so the present load sensor can be firmly fixed and the load transducer 21 can detect the original stressed status of the bone graft. Then the completely assembled spine specimen is installed in the material testing machine to simulate all possible motions of the spine. Therefore, referring to FIGS. 8(a)–8(d), with different preloaded conditions and spine implants, we can respectively obtain the data about the various loaded conditions of the load sensor. It is to be noticed that the horizontal axis represents the real force exerted on the spine construct and the longitudinal axis represents the load sensed by the sensor. Further, the line A is obtained from a first spine specimen with 3-level fixation, the line B is obtained from the first spine specimen with 5-level fixation, the line C is obtained from a second spine specimen with 3-level fixation, and the line D is obtained from the second spine specimen with 5-level fixation. According to the obtained data, what kind of spine implant would be selected and how the bone graft would be installed can be precisely ascertained.

b) On the other hand, during the clinical operation, after the excised part of the spine has been restoredly stretched, the present load sensor is grafted therein to sense the best original loaded condition thereat in order to implant the bone graft with best effects.

Figure 9:
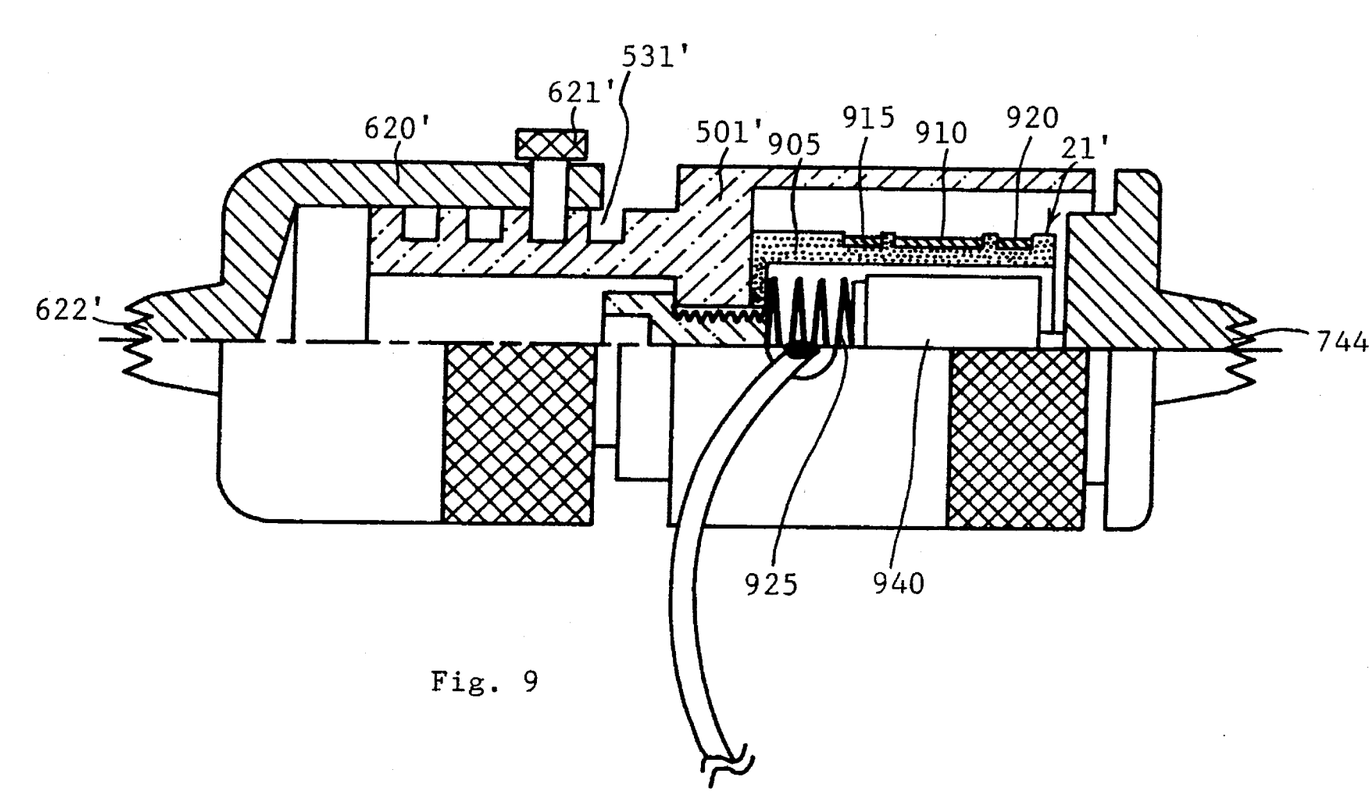
FIG. 9 shows another preferred embodiment of a load sensor according to the present invention.

FIG. 9 shows another preferred embodiment of a load sensor according to the present invention which is the same as the embodiment as shown in FIG. 2 with exceptions that the former has positioning devices 622' & 744' with claw-shaped ends rather than arc ends of those 622 & 744 of the latter, that a T-crosssectional piece 621' on the hollow tube 620' and a spiral groove 531' on the first post 501' of the former cooperatively perform the functions of the female screw thread 621 and the male screw thread 531 of the latter, and that the load transducer 21' of the former is inductive rather than strain gage-based as that 21 of the latter is. The load transducer 21' applies a linear variable differential transformer element including an isolating seat 905, a primary coil 910 mounted around the middle of the isolating seat 905, and two secondary coils 915, 920 respectively mounted around the seat 905 and disposed on two sides of the seat 905. There are also an iron core 940 movably mounted in the seat 905 and engageably with the positioning device 744', and a spring 925 connected to the iron core 940. When the iron core 940 is translated, the mutual inductance between the primary coil 910 and the two secondary coils 915, 920 will be changed and then there is a linear relation between the output signal and the position of the iron core 940 with respect to the seat 905. Thus, when the positioning device 744 is not applied with a force, the iron core 940 is positioned below the middle of the primary coil 910 and there is no output signal. When the load sensor is inserted between the two bones, the positioning device 744' will be subject to a force, so the spring 925 is compressively deformed and the iron core 940 is translated, and therefore there is an output signal generated. After being corrected, the output signal can help us to understand the real stressed status of the bone graft. While the present invention has been described in connection with what are presently considered to be the most practical and preferred embodiments, it is to be understood that the invention is not to be limited to the disclosed embodiments but on the contrary, is intended to cover various modifications and equivalent arrangements included within the spirit and scope of the appended claims which scope is to be accorded the broadest interpretation so as to encompass all such modifications and equivalent structures.

What is claimed is:

1. A load sensor adapted to be inserted between two bones of a mammal system for sensing a stress exerted on said load sensor comprising:
   a body;
   a load transducer mounted in said body for transducing a strain occurring thereon when said body is subjected to said stress into an electronic signal adapted to be transmitted to an analyzer for analyzing said stress exerted on said load sensor; and
   a length-adjusting means mounted on one end of said body for adjusting a length of said load sensor to make said load sensor firmly fixed between said two bones.

2. A load sensor according to claim 1 wherein said analyzer includes a computer.

3. A load sensor according to claim 1 wherein said analyzer includes an indicator.

4. A load sensor according to claim 1 wherein said body includes: a first post with a relatively smaller diameter and with a male screw thread; and a second post with a relatively larger diameter and generally connected coaxially to said first post.

5. A load sensor according to claim 4 wherein said second post contains therein said load transducer.

6. A load sensor according to claim 4 wherein said length-adjusting means includes:
   a hollow tube provided therein with a female screw thread engageable with said male screw thread for adjusting said length of said load sensor;
   a first positioning device mounted on one end of said hollow tube for permitting one end of said load sensor to be fixed with one of said two bones and for automatically producing an aligning effect.

7. A load sensor according to claim 6 wherein said second post and said hollow tube are respectively provided thereon with knurled surfaces for conveniently adjusting said length of said load sensor.

8. A load sensor according to claim 6, further comprising a fixing device including:
   a first disk held attached closely to said load transducer for protecting and shielding said load transducer from an undesired communication interference;
   a second disk having a relatively larger diameter and connected to said first disk for protecting said load transducer and a bottom of said body and for enlarging a force-receiving area; and
   a second positioning device connected to said second disk for permitting said load sensor to be fixed with another one of said two bones and for automatically providing an aligning effect.

9. A load sensor according to claim 8 wherein said first and second positioning devices are respectively protrusions with an arc end.

10. A load sensor according to claim 8 wherein said first and second positioning devices are respectively protrusions with a pointed end.

11. A load sensor according to claim 8 wherein said first and second positioning devices are respectively protrusions with a claw-shaped end.

12. A load sensor according to claim 1 wherein said length-adjusting means is fixed by a blocking device when said length is adjusted to a desired length.

13. A load sensor according to claim 12 wherein said blocking device includes at least one bolt.

14. A load sensor according to claim 13 wherein said body is processed to have a longitudinal plane surface in order that said male screw thread will not be damaged when said at least one bolt is to fix said length-adjusting means firmly, and superfluous blood, fat and flesh can be discharged along said longitudinal plane surface.

15. A load sensor according to claim 1 wherein said load transducer includes:
   a transducer body for resulting in said strain produced thereon when subject to said stress; and
   plural strain gages mounted on said transducer body for sensing said strain.

16. A load sensor according to claim 15 wherein said transducer body has a pair of planes on two opposite sides thereof and an egg-shaped hole therein.

17. A load sensor according to claim 16 wherein said egg-shaped hole and said pair of planes form thereby two thinnest portions of said transducer body.

18. A load sensor according to claim 17 wherein said two thinnest portions respectively have two outer surfaces and two inner surfaces.

19. A load sensor according to claim 18 wherein said plural strain gages include four strain gages.

20. A load sensor according to claim 19 wherein said four strain gages are respectively located on said surfaces.

21. A load sensor according to claim 1 wherein said load transducer is piezoelectric.

22. A load sensor according to claim 1 wherein said load transducer is inductive.

23. A load sensor according to claim 1 wherein said two bones are two parts of a broken bone.

24. A load sensor according to claim 1 wherein said two bones are two parts of an ill bone.

25. A load sensor according to claim 24 wherein said two bones are partially separated.

26. A load sensor according to claim 1 wherein said two bones are two segments of a patient's spine.

* * * * *